United States Patent
Foti et al.

(10) Patent No.: US 7,601,805 B2
(45) Date of Patent: Oct. 13, 2009

(54) PHOTOPROTEIN WITH IMPROVED BIOLUMINESCENCE

(75) Inventors: Maria Foti, Milan (IT); Stefan Lohmer, Milan (IT)

(73) Assignee: AXXAM S.R.L., Milan (IT)

( * ) Notice: Subject to any disclaimer, the term of this patent is extended or adjusted under 35 U.S.C. 154(b) by 150 days.

(21) Appl. No.: 10/530,658

(22) PCT Filed: Oct. 21, 2003

(86) PCT No.: PCT/EP03/11626

§ 371 (c)(1),
(2), (4) Date: Apr. 7, 2005

(87) PCT Pub. No.: WO2004/035620

PCT Pub. Date: Apr. 29, 2004

(65) Prior Publication Data

US 2007/0065818 A1   Mar. 22, 2007

(30) Foreign Application Priority Data

Oct. 21, 2002   (EP) ................................. 02023452

(51) Int. Cl.
| | |
|---|---|
| C07K 14/00 | (2006.01) |
| C07H 21/02 | (2006.01) |
| C07H 21/04 | (2006.01) |
| C12P 21/06 | (2006.01) |
| C12N 1/20 | (2006.01) |
| C12N 1/00 | (2006.01) |
| C12N 5/00 | (2006.01) |
| C12N 5/02 | (2006.01) |
| C12N 5/04 | (2006.01) |
| C12N 5/10 | (2006.01) |
| C12Q 1/00 | (2006.01) |

(52) U.S. Cl. ...................... 530/350; 536/23.1; 536/23.4; 536/23.5; 435/69.1; 435/252.3; 435/254.11; 435/254.2; 435/325; 435/4; 435/419

(58) Field of Classification Search ...................... None
See application file for complete search history.

(56) References Cited

OTHER PUBLICATIONS

Ngo et al., in The Protein Folding Problem and Tertiary Structure Prediction, 1994, Merz et al. (ed.), Birkhauser, Boston, MA, pp. 433 and 492-495.*
Witkowski et al., Biochemistry, 38, 11643-11650, 1999.*
Wishart et al., Journal of Biological Chemistry, vol. 270, No. 45, pp. 26782-26785, 1995.*
Kisselev, Structure, vol. 10, pp. 8-9, 2002.*
Liu et al. (Structure of the Ca2+-regulated photoprotein obelin at 1.7 Å resolution determined directly from its sulfur substructure, Protein Science, vol. 9 Issue 11, pp. 2085-2093).*
Svetlana V. Markova, et al.; "Obelin from the Bioluminescent Marine Hydroid Obelia Geniculata: Cloning, Expression, and Comparison of Some Properties with Those of Other $CA^{2+}$-Regulated Photoproteins", Feb. 19, 2002; Biochemistry 2002, vol. 41, No. 7, pp. 2227-2236.
Boris A. Illarionov, et al.; "Recombinant Obelin: Cloning and Expression of cDNA, Purification, and Characterization as Calcium Indicator"; Methods in Enzymology; vol. 305, 2000, pp. 223-249.
Frederick I. Tsuji, et al.; "Molecular Evolution of the $Ca^{2+}$-Binding Photoproteins of the Hydrozoa"; Photochimistry and Photobiology, vol. 62, No. 4, 1995, pp. 657-661.
S.V. Matveev, et al.; "Genetically Engineered Obelin as a Bioluminescent Label in an Assay for a Peptide"; Analytical Biochemistry, vol. 270, No. 1, May 15, 1999, pp. 69-74.

* cited by examiner

*Primary Examiner*—Suzanne M. Noakes
*Assistant Examiner*—Jae W Lee
(74) *Attorney, Agent, or Firm*—Arent Fox LLP

(57) ABSTRACT

Disclosed is a photoprotein with improved luminescent activity, the use thereof as calcium indicator and in cell-based assays for the detection and measurement of intracellular calcium.

19 Claims, 5 Drawing Sheets

US 7,601,805 B2

PHOTOPROTEIN WITH IMPROVED BIOLUMINESCENCE

CROSS-REFERENCE TO RELATED APPLICATION

This application is a National Stage entry of International Application No. PCT/EP03/11626, filed Oct. 21, 2003, the entire specification claims and drawings of which are incorporated herewith by reference.

The present invention provides a chimeric photoprotein with improved luminescent activity, the use thereof as calcium indicator in reporter gene systems and in cell-based assays for the detection and measurement of intracellular calcium.

BACKGROUND OF THE INVENTION

Bioluminescence is the capacity of living organisms to emit visible light through a variety of chemiluminescent reaction systems. Bioluminescence reactions require three major components: a luciferin, a luciferase and molecular oxygen. However other components may also be required in some reactions, including cations ($Ca^{++}$ and $Mg^{++}$) and cofactors (ATP, NAD(P)H). Luciferases are enzymes that catalyse the oxidation of a substrate, luciferin, and produce an unstable intermediate. Light is emitted when the unstable intermediate decays to its ground state, generating oxyluciferin. There are many different unrelated types of luciferin, although many species from at least seven phyla use the same luciferin, known as coelenterazine, which contains a ring formed by three amino acids (2 tyrosines, and a phenylalanine). In some animals (e.g. jellyfish) the luciferin/luciferase system can be extracted in the form of a stable "photoprotein" which emits light upon calcium binding. Photoproteins differ from luciferases in that they are stabilized oxygenated intermediate complexes of luciferase and luciferin. Photoproteins are present in many marine coelenterates and allow these organisms to emit light for a variety of purposes including breeding, feeding, and defense (1). While bacteria emit light continuously, in many other organisms luminescence occurs as flashes, typically of 0.1-1 sec. duration. This requires a rapid switch on/off of the enzymatic reaction and the presence of reagents appropriately sequestered and ready to quick mobilization. In coelenterates, flashing is caused by calcium entry. The calcium binding sites of photoproteins are homologous to calmodulin. In the presence of calcium, photoproteins emit visible light through an intramolecular reaction. There are many luminescent organisms, but only seven photoproteins, namely Thalassicolin (2,3), Aequorin (4-6), Mitrocromin (syn. Halistaurin) (7,8), Clytin (syn. with Phialidin) (8,9) Obelin (2,6,10,11), Mnemiopsin (12,13), and Berovin (12, 13), have been isolated so far. All these proteins are complexes of an apoprotein, an imidazopyrazine chromophore (coelenterazine), and oxygen. Their structures are highly conserved, especially in the region containing the three calcium binding sites (EF-hand structures). These EF-hand structures are characteristic of the calcium-binding protein family. The photoprotein emits light upon reaction with calcium which tightly binds to the EF-hand pocket. The reaction is a single turnover event and results in the release of $CO_2$ and emission of light in the blue region ($\lambda_{max}$=470 nm). The term "photoprotein" identifies the luciferin-bound polypeptide, which is capable of luminescence, while "apophotoprotein" is used to indicate the protein without luciferin.

The most studied photoproteins are Aequorin, isolated from *Aequorea Victoria* (14) and Obelin, isolated from *Obelia longissima* (15). Upon binding $Ca^{++}$ Aequorin undergoes a conformational change converting itself into an oxygenase (luciferase), which then catalyzes the oxidation of coelenterazine by the bound molecular oxygen. The blue fluorescent protein is made up of coelenteramide, which is an oxidation product of coelenterazine, not covalently bound to apophotoprotein. The photoprotein may be regenerated from the apophotoprotein by incubation with coelenterazine, molecular oxygen, EDTA and 2-mercaptoethanol or dithiothreitol. Since coelenterazine is the common luminescent substrate used by the photoproteins Aequorin, Mitrocomin, Clytin and Obelin, the light-emitting reaction is likely the same in these four photoproteins (16). The recent acquisition of the primary structure and of the crystallographic data of Aequorin and Obelin gave rise to additional information on their function. Native Obelin from the hydroid *Obelia longissima* is a single-chain protein of 195 amino acid residues (aa) with an approximate molecular mass of 20 kDa that contains the noncovalently bound chromophoric group coelenterazine. The analysis of the primary structures of Clytin shows that it contains 189 aa and belongs to the family of photoproteins. The hydrozoan $Ca^{++}$-binding photoprotein, however, differ from other $Ca^{++}$-binding proteins such as calmodulin and troponin C by a relatively high content of cysteine, histidine, tryptophan, proline and tyrosine residues.

Studies of Obelin structure and function are reported in Bondar V S et al., Biochemistry (2001), 66(9):1014-8, Vysotski E S et al., (2003), 42(20): 6013-24 and Deng L. et al., FEBS Lett. (2001), 506(3): 281-5. The two latter, in particular, describe bioluminescence and emission properties of a W92F obelin mutant.

Photoproteins are widely used in reporter gene technology to monitor the cellular events associated with signal transduction and gene expression.

The study of cellular events and their regulation requires sensitive, non invasive analytic methods. Photoproteins and in general bioluminescence are excellent reporter systems as they have virtually no background in contrast to fluorescence systems.

Photoproteins have been expressed in mammalian cells to monitor calcium changes in response to different stimuli. Intracellular calcium concentration can be measured by adding coelenterazine cofactor to mammalian cells expressing the photoprotein and detecting photon emission, which is indicative of intracellular calcium concentration.

DESCRIPTION OF THE INVENTION

It has now been found that by chimerization of Obelin protein (Apobelin) through replacement of a region thereof comprised between the first two calcium binding sites, with a corresponding region of a photoprotein selected from Clytin, Aequorin, Thalassicolin, Mitrocromin, Mnemiopsoin and Berovin, a novel photoprotein with improved bioluminescence is obtained.

As used herein, Obelin may refer to any of the photoproteins isolated from different species of *Obelia*, including *Obelia longissima* and *Obelia geniculata* (17). Reference Obelin nucleotide and amino acid sequences are listed in SEQ ID N. 1 and 2, respectively. Reference amino acid and nucleotide sequences of Clytin, Mitrocromin and Aequorin are deposited at GenBank accession numbers Q08121, P39047, AAA27720 and, respectively, L13247, L31623, L29571, whereas sequences for Thalassicolin, *Mnemiopsis* and Berovin are described in references 2, 3, 12 and 13.

A "corresponding region or fragment", as used herein, means any amino acid sequence, within the selected photoprotein, matching Obelin sequence in respective sequence alignments with the exception of at least 1, preferably at least 5, more preferably at least 10 amino acid residues, which are not conserved in the relevant proteins (Obelin and selected photoprotein), said region or fragment preferably spanning residues 42-122, more preferably residues 50-95, as referred to Obelin sequence.

According to a preferred embodiment of the invention, the chimeric protein is obtained by replacing residues 50 to 94 of Obelin amino acid sequence with a fragment of Clytin sequence extending from residue 53 to 97. The photoprotein thus obtained, which has been named "Photin", has the amino acid sequence of SEQ ID N. 3.

The chimeric proteins of the invention can be further modified by deletion, addition or substitution of one or more amino acid residues, provided that the activity profile of the photoprotein, in terms of light-emission and calcium-responsiveness, is maintained or increased. Particularly preferred are the substitutions at positions 55, 66, 67, 73, 74, 75, 78, 83, 84, 87, 89 and 94, as referred to obelin sequence.

As shown by in vitro studies, Photin produces an intense bioluminescence in response to calcium stimulation, which is generally higher than that observed with natural photoproteins.

For the preparation of the chimeric photoproteins, a recombinant DNA construct bearing portions of the coding sequences of Obelin and of a selected photoprotein other than Obelin is prepared using conventional genetic engineering, the resulting chimeric product is inserted in a vector, expressed in a suitable host and then isolated and purified. For example, the cDNAs coding for Obelin and for a different photoprotein can be amplified by PCR or constructed in vitro with synthetic oligonucleotides and the products can be recombined making use of suitable restriction sites, naturally occurring or artificially introduced into the oligonucleotides used for amplification or for in vitro construction. The expression vector can contain, in addition to the recombinant construct, a promoter, a ribosome binding site, an initiation codon, a stop codon or a consensus site for transcription enhancers. The vector can also comprise a selection marker for isolating the host cells containing the DNA construct. Suitable vectors are for example yeast or bacteria plasmids, bacteriophages, viruses, retroviruses or DNA. The vectors carrying the recombinant construct can be introduced in the host by means of conventional techniques. Host cells can be prokaryotic or eukaryotic, such as bacteria, yeasts or mammal cells. The preferred hosts for photoprotein expression/production are mammalian cells, including cells of epithelial or lymphoblast origin such as Hek-293, CHO-K1, HepG2 and HL-60. These cells may express the apophotoprotein in the cytoplasm (18), in the mitochondria, by addition of a mitochondrial targeting sequence to the photoprotein, or in any other cell compartment (19-21). Alternatively, non mammalian cells, such as bacteria or fungi, can be employed. Once the host cell type has been selected, the genetic constructs can be introduced by calcium phosphate precipitation, electroporation or other conventional techniques. After transfection, cells are grown in suitable media and screened for appropriate activities. The photoprotein of the invention may be isolated and purified with conventional procedures, such as extraction, precipitation, chromatography, affinity chromatography, electrophoresis.

Point mutations can be introduced into the chimeric product by means of overlap extension PCR.

To produce Photin, the NdeI/MunI fragment of Obelin gene was replaced with a fragment of 135 nucleotides corresponding to Clytin coding sequence ranging from nucleotide 156 to 291.

In a further aspect, the invention is directed to a nucleic acid molecule encoding the chimeric proteins herein disclosed. DNA coding sequences can be modified by virtue of genetic code degeneracy, for example changing the codon usage to improve the expression in heterologous systems.

In a preferred embodiment of the invention, the DNA sequence coding for the Photin protein is selected from SEQ ID No. 4 and 5.

To test whether the chimeric product was functional, in vitro transcription and translation experiments were performed in a cell-free wheat germ translation system in the presence of coelenterazine. In these experiments, active photoprotein formation is recorded by testing luminescence from the translation mixture, after addition of calcium ions. To correlate the measured luminescence with the amount of protein produced, a translation reaction was carried out in the presence of $^{35}$S-Methionine. The amount of newly synthesized polypeptide was determined by measurement of $^{35}$S-Methionine incorporation into the trichloroacetic insoluble fraction. The results of these experiments demonstrate the sensitivity and effectiveness of Photin in generating bioluminescence in response to calcium-ions stimulation.

In a further embodiment of the invention, the chimeric proteins here provided are used as calcium indicators, especially for the measurement of intracellular calcium concentration. In a typical assay, a cofactor such as coelenterazine is added to mammalian cells expressing the photoprotein and light emission is recorded by methods known in the art, for example using a commercially available luminometer.

Cells expressing both the photoprotein and a receptor involved in intracellular calcium mobilization can be used to test candidate molecules for their effects on receptor modulation. The chimeric photoprotein of the invention can be used in a variety of cell-based functional assays that utilize measurement of intracellular calcium to evaluate the activity of proteins, particularly G-protein coupled receptors (GPCRs) and plasma membrane ion channels. Although the large and rapid increase in intracellular calcium concentration following GPCRs and ion channel stimulation can be detected by various reporters such as calcium-sensitive fluorescent dyes, the use of bioluminescent photoproteins (22) is preferred as their background is virtually absent in contrast to fluorescent dyes; moreover, calcium measurement with photoproteins, besides producing rapid signals, generates a high signal-to-noise ratio with a broad range of detection sensitivity (22, 23). Cell-based functional assays typically comprise adding an appropriate agonist to a culture of cells expressing both GPCRs or ion channels and the photoprotein, and then determining any variation of calcium concentration, for example a calcium increase induced by either rapid influx from extracellular sites or release from intracellular stores (18), through measurements of the photoprotein activity.

The use of cells which express both Photin and a receptor involved in the modulation of intracellular calcium concentration provides a valid system for the screening of compounds for their effects on the release of intracellular calcium. High throughput screening assays can also be designed using a photoprotein according to the invention as reporter system. The sensitivity of the system as well as its high signal to noise ratio allow the use of small assay-volumes.

In a further embodiment, a photoprotein according to the invention is conjugated to a molecule of analytical, diagnostic or therapeutic interest and the conjugation product is used in a competitive solid-phase immunoassay to determine the amount of that molecule in biological samples. For example, the photoprotein may be chemically conjugated to a hormone protein and used in a solid-phase immunoassay with hormone-specific antibodies to determine the salivary levels of the hormone (24). In a yet further embodiment, a fusion product between a photoprotein according to the invention and a different (poly)peptide, such as a hormone, an antigenic peptide, light or heavy chain immunoglobulin, avidin, streptavidin or protein A, is produced with known techniques of genetic engineering, as disclosed in U.S. Pat. No. 6,087,476 (which is hereby incorporated by reference), and used in immunodiagnostic or imaging processes.

The following examples illustrate the invention in greater detail.

EXAMPLES

1. In Vitro Transcription/Translation of Photoprotein DNA

Translation of the photoproteins was carried out in the wheat germ cell-free system (TNT kit, Promega), following the general instructions of the supplier. Approximately 2 µg of DNA was used for each in vitro transcription/translation reaction mix. The translation volume (50 µl) included 25 µl of the wheat germ extract, 2 µl of the reaction buffer, a mixture of amino acids except for Methionine, Rnasin and Coelenterazine (40 µM), T7 Polimerase. The mixture contained also $^{35}$S-Methionine (specific activity 1000 Ci/mmol). $^{35}$S-Methionine was used to determine the amount of photoprotein synthesized in vitro. To this end, 5 µl from each sample of the translation mixture were TCA precipitated in ice for 30 min., filtered, washed with cold 5% TCA, methanol, dried and placed into counter vials.

The amounts of Photin and Obelin produced in the cell-free system are shown in Table I.

TABLE I

Inclusion of Radioactive Label into Products of Translation of the photoproteins

| Added DNA | Obelin (1 µg) | Photin (1 µg) | Aequorin (1 µg) |
|---|---|---|---|
| $^{35}$S Counting upon 90 min Translation (cpm) | 8169 | 8290 | 13049 |

2. Photoprotein Assay 5 and 10 µl of the translation mixture were directly mixed with 95-90 µl of PBS solution in a 96 well plate which was mounted into the Luminometer (Berthold). To trigger photoprotein light emission, 50 µl solution (50 mM $CaCl_2$) were injected into the well and luminescence recorded for 10 seconds.

Figure 1:
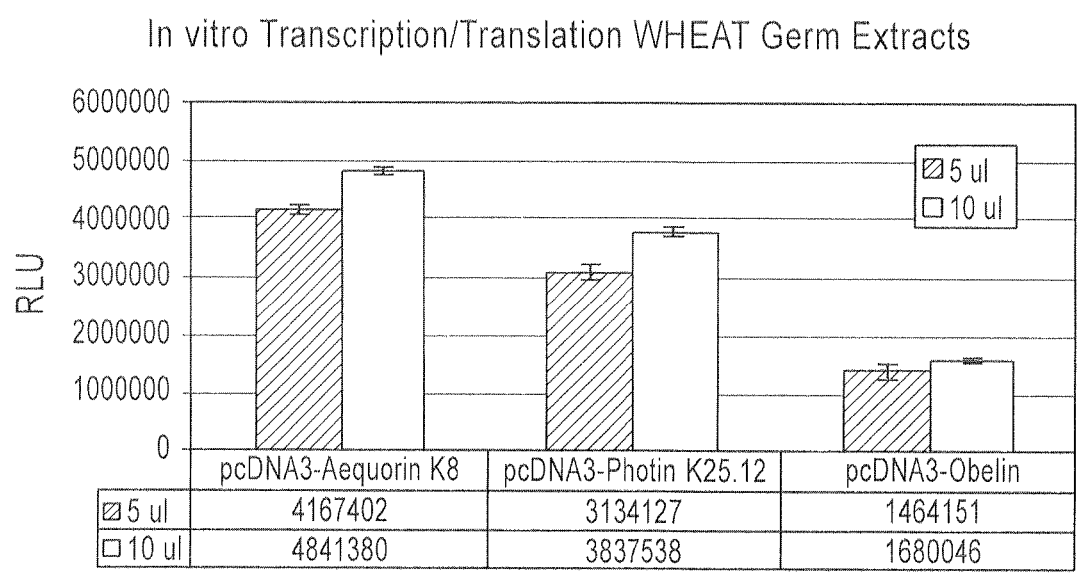
FIG. 1 Calcium-induced bioluminescence of newly synthesized photoproteins. The photoproteins were translated in a wheat germ cell-free system in the presence of coelenterazine. All translation mixture aliquots were incubated for 2 hrs in the dark at 30° C. The reaction was loaded with $CaCl_2$ 50 mM and luminescence recorded for 10 seconds.
Figure 2:
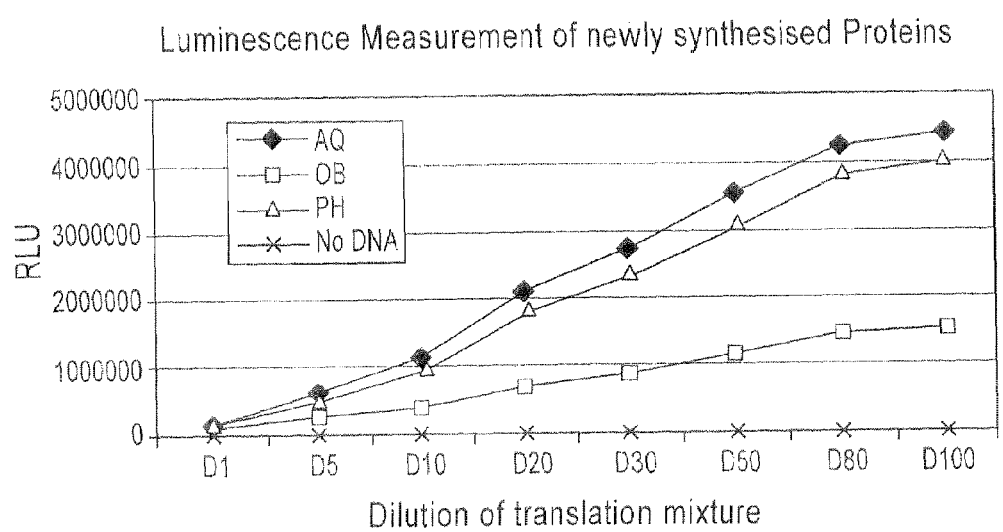
FIG. 2 Photoproteins DNA translation in the presence of coelenterazine, with luminescence measured by diluting the reaction mixture. AQ:Aequorin, PH:Photin, OB:Obelin.

The results of the in vitro translation of Photin, Obelin and Aequorin DNA are shown in FIG. 1. The luminescence measurements obtained by diluting the photoprotein in vitro translation reactions are shown in FIG. 2. The comparison of luminescence data with TCA counts obtained during translation with different amounts of Photin and Obelin DNA is shown in Table II (the measured luminescence is proportional to the amount of photoprotein newly synthesized).

TABLE II

Content of Radiolabeled photoprotein and its Luminiscence in the Translation Mixture

| | Obelin | | Photin | |
|---|---|---|---|---|
| DNA (ng) | TCA Counts (Cpm/µl) | Luminescence (RLU/µl) | TCA Counts (cpm/µl) | Luminescence (RLU/µl) |
| 250 | 2722 | 358944 | 2927 | 990308 |
| 125 | 2396 | 271952 | 2094 | 858046 |
| 63 | 1030 | 139241 | 807 | 339348 |
| 31 | 579 | 41970 | 502 | 88326 |
| 16 | 265 | 13482 | 196 | 30617 |

Figure 3:
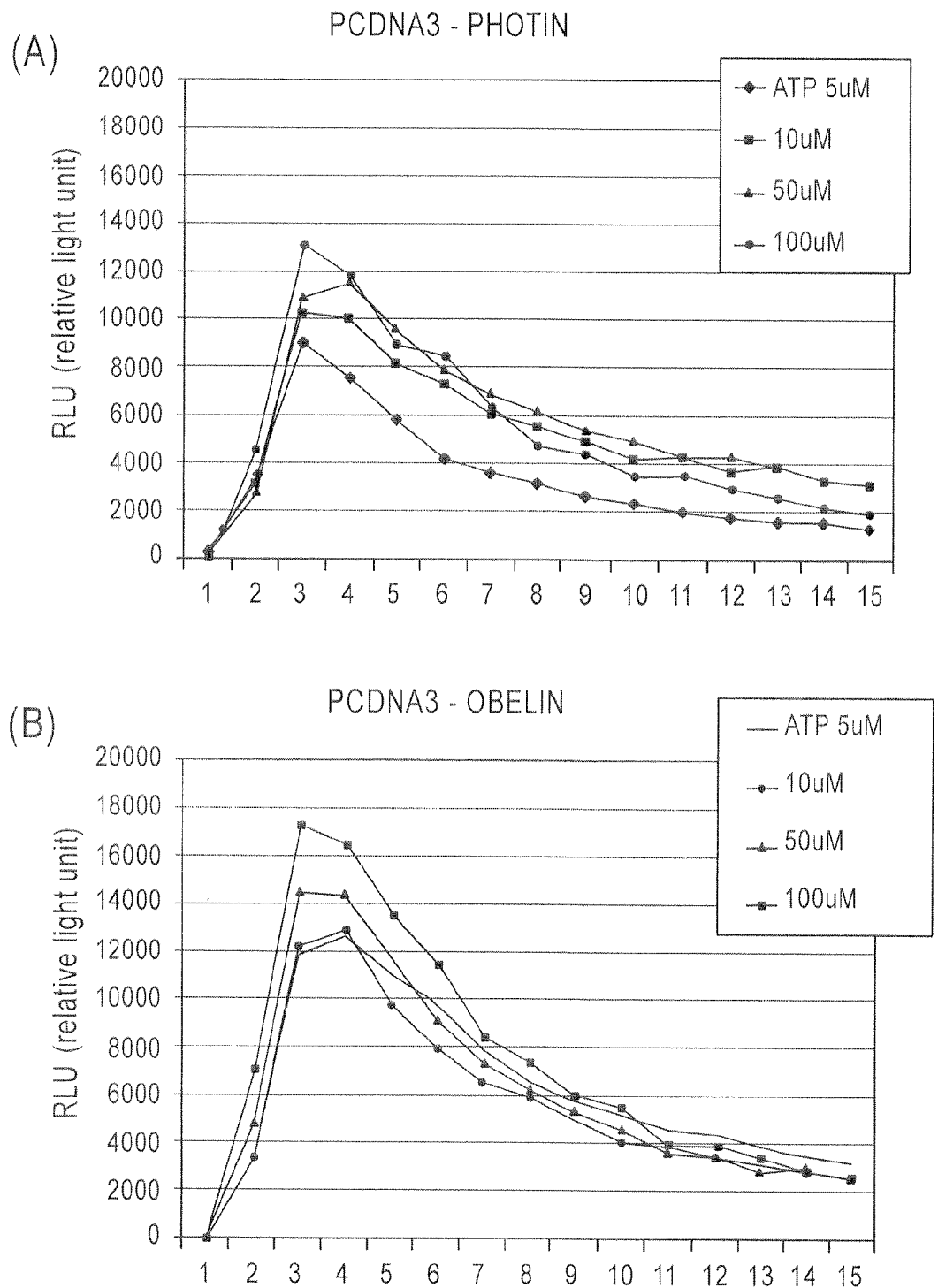
FIG. 3 (A) ATP dose dependent light emission upon stimulation of the endogenous ATP receptor expressed by CHO-K1 cell transfected with photin DNA. Cell transfection, harvesting, and Photin expression were performed as described in Example 1. Cells were treated with two different concentration of ATP. (B) The CHO-K1 cells transfected with Obelin DNA were used as positive control. Luminescence is expressed in RLU (relative light units).

3. Examples of Cell-Based Functional Assays 3.1 Photin-expressing clones have been obtained by transfection of CHO-K1 cells (Materials and Methods). Two days after transfection the cells were trypsinized and diluted 10 or 100 times. Once the cells were grown up to well isolated colonies, the colonies were transferred to new plates and selected on the basis of their functional response (luminescent signal) to different concentration of ATP, which is known to stimulate the CHO endogenous receptor and to rise the cytoplasmic $Ca^{++}$ concentration. At the end of each experiment, cells were lysed by perfusion of a solution containing TritonX-100 and $CaCl_2$. The active photoprotein was reconstituted incubating the cells with 10 µM coelenterazine diluted in PBS containing 2 mM calcium, in the dark at 37° C. in a 5% CO2 atmosphere for 3 hrs. For light emission measurement, cells were lysed in the presence of calcium and the emitted luminescence recorded. The number of photons emitted during the first 10 seconds was integrated by the luminometer and visualized on the screen. Cells transfected with an empty plasmid or untransfected (data not shown) did not increase photon-emission. To detect changes in calcium concentrations, 10, 50 and 100 µM ATP were injected and the kinetics of calcium response determined. The curve obtained is shown in FIG. 3 (A). A cell line expressing the photoprotein Obelin was used as positive control FIG. 3 (B).

Figure 4:
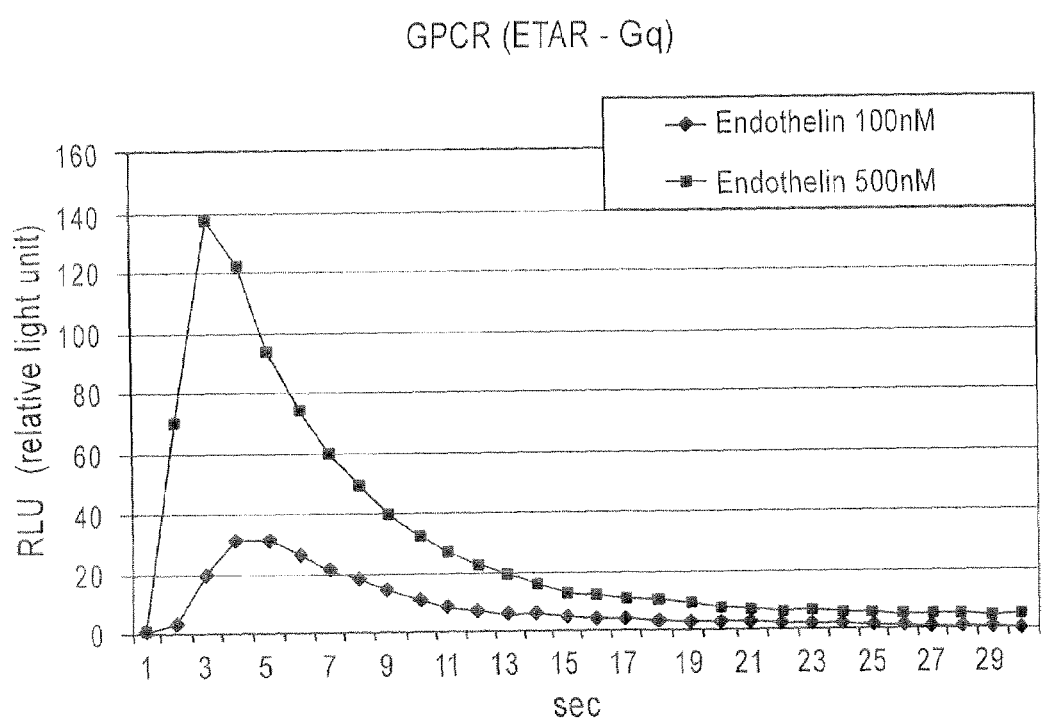
FIG. 4 Dose-dependent curve of Photin activity in CHO-K1 cells transfected with both the Endothelin A receptor and Photin. The receptor was activated by injection of endothelin at a concentration of 100 and 500 nM.

3.2 A CHO cell line expressing endothelin A receptor and Photin was established. Upon stimulation with an agonist, this receptor induces an increase in intracellular calcium concentration which is measured by Photin luminescence. Cells were cultivated as a monolayer in DMEM/F12 medium containing 10% Fetal Bovine Serum (FBS) in a 96-well plate. On the day of the experiment, the culture medium was removed and cells were incubated with 10 µM Coelenterazine in PBS for at least 3 h. Endothelin peptide was diluted in PBS at a concentration of 100 and 500 nM. Approximately 50 µl of endothelin were injected into each well and the response measured. The emitted light was immediately recorded over a period of 30 seconds. The dose-dependent response to endothelin is reported in FIG. 4.

Figure 5:
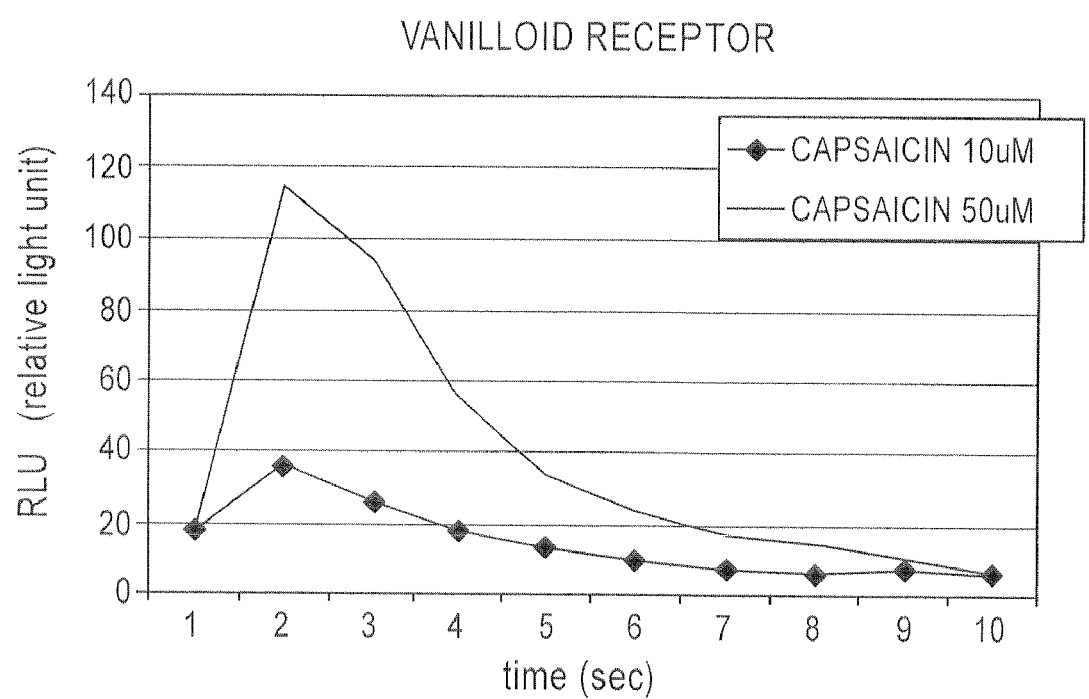
FIG. 5 Dose-dependent curve obtained from cells expressing the photoprotein Photin and the rat vanilloid receptor 1 (VR1). The specific agonist, capsaicin, was used at a concentration of 10 and 50 µM.

3.3 CHO cell lines expressing both Apophotin and the rat VR1 capsaicin receptor—a calcium-permeable ion channel—were grown to 80-95% confluence in tissue culture flasks and harvested by trypsinization. Cells were dispensed at 10,000 cells/well in a 96-well white plates in growth medium and incubated overnight at 37° C. in a humidified incubator at 5% $CO_2$. For luminescence experiments, the cells were loaded with coelenterazine 10 µM for 3 h at 37° C., 5% $CO_2$. Calcium response was stimulated by addition of 10 and 50 µM capsaicin to each well. The kinetics of flash luminescence was followed using Labsystem Luminoskan Ascent, which injects reagents and records light emission from each single well. Addition of capsaicin caused a rapid and transient luminescence signal within 30 seconds, with a peak level occurring in about 10 seconds (FIG. 5).

Materials and Methods
Reagents

Restriction enzymes were purchased from New England Biolabs and used according to supplier's instructions. Rnasin and the TNT kit for in vitro Transcription and Translation were from Promega (Madison, Wis.). Pfu Turbo polymerase, reagents for PCR, and competent cells of *E. coli* strains XL-1Blue and BL21, were from Stratagene (La Jolla, Calif.). Oligonucleotides were purchased from Primm (Milan). Coelenterazine was from Prolume Ltd. (Pittsburgh, Pa.). All other chemicals were from standard sources and were of reagent grade or better.

Assembly PCR for Single Step Synthesis of Obelin DNA Sequences

Four steps are required for PCR assembly: oligo synthesis, gene assembly, gene amplification and cloning. We synthesized 30 oligos, 40 nt in length, which collectively encode both strands of the Obelin gene sequence. The overlap of complementary oligos is 20 nt. Equal volumes drawn from each of the 30 oligo solutions were combined to a final concentration of approximately 250 µM of mixed oligos, prior to a 250-fold dilution in 20 µl of Geneamp XL PCR mix (Perkin Elmer). The amplification process has been carried out in three stages. The first step was carried out with pooled oligos as follows: 40° C. for 2 min, then addition of polymerase, 72° C. for 10 sec., then 40 cycles (94° C. for 15 s, 40° C. for 30 sec. and 72° C. for 10 sec.). The reaction mixture was diluted three-fold with fresh PCR and polymerase mix. The second stage was: 25 cycles (94° C. for 15 s, 40° C. for 30 s and 72° C. for 45 s). The reaction was again diluted threefold in complete PCR mix. The conditions for the third stage were: 20 cycles (94° C. for 15 s, 40° C. for 30 s and 72° C. for 70 s). The reaction products were analyzed by 1% agarose-gel electrophoresis, and the specific fragment cloned into the pcr-Blunt vector for further cloning steps. The plasmid has been called pcr-OB. The fidelity of the PCR reactions was confirmed by dideoxy sequencing.

Construction of the Chimeric Protein

Four couples of oligos have been designed from the Clytin gene sequence. The region between EF-hand I and EF-hand II have been chosen for gene chimerization. The oligonucleotide primers were the following:

```
Clyt-4
5'-AATTCTTTCCATCCATCAACAAAAGCTGGGAATTCGACTTCTTTAC
CATAATCCATACCAATC-3'
(SEQ ID NO: 9)

Clyt-3
5'-AAAGATTGGTATGGATTATGGTAAAGAAGTCGAATTCCCAGCTTT
TGTTGATGGATGGAAAG-3'
(SEQ ID NO: 8)

Clyt-2
5'-TTTTTGAAGAAAGCTTCGACAGCATCCTGGTGACGTTTGGTCTGTT
CTGGTGTTGCTCCAAGTTTGGCGCA-3'
(SEQ ID NO: 7)

Clyt-1
5'-TATGCGCCAAACTTGGAGCAACACCAGAACAGACCAAACGTCAC
CAGGATGCTGTCGAAGCTTTCTTCAA-3'
(SEQ ID NO: 6)
```

The annealed oligos have been cloned into the NdeI/MunI unique sites in the pcr-OB vector. The plasmid containing the chimeric gene product is called pcr-Photin. Photin DNA has been further subcloned into the pcDNA3 vector which contains the T7 promoter.

PCR-Based Codon Usage Change

The technique of overlap extension PCR was employed to produce the Obelin mutant. Six couples of primers were designed with ten different point mutations which produce ten different codon usage changes. To amplify DNA fragments used to overlap extension, PCR reactions were carried out with 2.5 units of Pfu polymerase, 50 ng of DNA template, 250 µM each dNTP, and 50 pmol of each primer in a total volume of 100 µl. The cycling parameters employed were 94° C. for 1 min, 45° for 1 min, and 72° C. for 1 min 30 s for the first 10 cycles, followed by 20 cycles with an annealing temperature of 50° C. The site-specific mutations were confirmed through DNA sequencing performed at Primm (Milan). All molecular procedures were conducted using standard protocols.

CHO Cell Culture

All cells were cultured under standard humidified conditions at 37° C. and 5% CO2. CHO cells were maintained in DMEM/F12+ FBS 10%+Pen/Strep+G418 0.5 mg/ml+Pyruvate 1.6 mM+NaHCO₃ 0.2%, all reagents were from Life Technologies. DNA transfection was performed when these cells were grown to a 70% to 80% confluence on the plates.

REFERENCES

1. Kendall, J. M., and Badminton, M. N. (1998). *Aequorea victoria* bioluminescence moves into an exciting new era. Trends Biotechnology. 16(5):216-24.
2. Campbell, A. K., Hallet, R. A., Daw, M. E., Ryall, R. C., Hart and Herring P. J. (1981). Application of the photoprotein obelin to the measurement of free $Ca^{++}$ in cells. In Bioluminescence and Chemiluminescence, basic Chemistry and Analytical applications (Edited by M. A. deLuca and W. D. McElroy), pp. 601-607. Academy Press, New York.

3. Herring, P. J. (1979) Some features of the bioluminescence of the radiolarian *Thalassicola* sp. Mar. Biol. 53, 213-216.
4. Shimomura, O., Johnson F. H., and Saiga, Y (1962) Extraction, purification and properties of aequorin, a bioluminescent protein from the luminous hydromedusan, *Aequorea*. J. Cell. Comp. Physiol. 59, 223-239.
5. Shimomura, O., Johnson F. H., and Saiga, Y (1963) Further data on the bioluminescent protein, aequorin. J. Cell. Comp. Physiol. 62, 1-8.
6. Morin, J. G. and Hastings J. W. (1971) Biochemistry of the bioluminescence of colonial hydroids and other coelenterates. J. Cell. Physiol. 77, 305-311.
7. Shimomura, O., Johnson, F. H. and Saiga, Y. (1963) Extraction and properties of halistaurin, a bioluminescent protein from the hydromedusan *Halistaura*. J. Cell. Physiol. 62, 9-15.
8. Shimomura, O., and Shimomura, A. (1985) Halistaurin, phialidin and modified forms of aequorin as $Ca^{++}$ indicator in biological systems. Biochem. J. 228, 745-749.
9. Levine, L. D., and Ward, W. W. (1982) Isolation and characterization of a photoprotein "phialidin" and a spectrally unique green-fluorescent protein from the bioluminescent jellyfish *Phialidium gregarium*. Comp. Biochem. Physiol. 72B, 77-85.
10. Morin, J. G. and Hastings (1971) Energy transfer in a bioluminescent system. J. Cell. Physiol. 77, 313-318.
11. Campbell, A. K. (1974) Extraction, partial purification and properties of obelin the calcium-activated protein from the hydroid *Obelia geniculata*. Biochem. J. 143, 411-418.
12. Ward, W. W. and Selinger (1974) Extraction and purification of calcium-activated photoprotein from the ctenophores *Mnemiopsis* sp. and *Bern ovata*. Biochemistry 13, 1491-1499.
13. Ward, W. W. and Seliger H. H. (1974) Properties of mnemiopsin, and berovin, calcium-activated photoproteins from the ctenophores *Mnemiopsis* sp. and *Beroë ovata*. Biochemistry 13, 1500-1510.
14. Johnson, F. H. and Shimomura, O. (1978) Introduction to the bioluminescence of medusae, with special reference to the photoprotein aequorin. Methods Enzymol. 57, 271-291.
15. Illarionov B A, Bondar V S, Illarionova V A, Vysotski E S. Sequence of the cDNA encoding the $Ca^{++}$-activated photoprotein obelin from the hydroid polyp *Obelia longissima*. Gene. 1995 14; 153(2):273-4.
16. Blinks, J. R., Weir, W. G., Hess, P. and Prendergast, F. G. (1982). Measurement of $Ca^{++}$ concentrations in living cells. Prog. Biophys. Mol. Biol. 40, 1-114.
17. Markova S V, Vysotski E S, Blinks J R, Burakova L P, Wang B C, Lee J., (2002) Obelin from the bioluminescent marine hydroid *Obelia geniculata*: cloning, expression, and comparison of some properties with those of other Ca2+-regulated photoproteins. Biochemistry. 2002 Feb. 19; 41(7):2227-36.
18. Button D, Brownstein M. (1993) Aequorin-expressing mammalian cell lines used to report $Ca^{++}$ mobilization. Cell Calcium. October; 14(9):663-71.
19. Mattheakis, L., and Ohler, L. D. (2002) Seeing the light: Calcium imaging in cells for drug discovery. Drug Discovery Today S, 15-19
20. Stables J, Green A, Marshall F, Fraser N, Knight E, Sautel M, Milligan G, Lee M., Rees S. (1997). A bioluminescent assay for agonist activity at potentially any G-protein-coupled receptor. (1997) Anal Biochem 1; 252(1):115-26.
21. Brini M., Pinton P., Pozzan T., Rizzuto R. (1999). Targeted recombinant aequorins: tools for monitoring $Ca^{++}$ in the various compartments of a living cell. Microsc. Res. Tech. 46, 380-389.
22. Creton R., Kreiling J. A., Jaffe L F. (1999) Calcium imaging with chemiluminescence. Microsc. Res. Tech. 46, 390-397.
23. Shimomura, O. et al. (1993) Light-emitting properties of recombinant semi-synthetic Aequorins and recombinant fluorescin-conjugated Aequorin for measuring cellular calcium. Cell Calcium 14, 373-378.
24. Mirasoli, M. et al. (2002) Bioluminescence immunoassay for cortisol using recombinant aequorin as a label. Analytical Biochemistry 306, 204-211.

---

The invention claimed is:

1. A chimeric photoprotein obtained by replacing a region of Obelin protein of SEQ ID NO:2 with a corresponding region of Clytin photoprotein, wherein said region consists of residues 43 to 121 of SEQ ID NO: 2, wherein said chimeric photoprotein is bioluminescent and wherein said corresponding region of Clytin photoprotein is the same corresponding region of the Obelin protein sequence that is to be replaced with the exception of up to 5 amino acid residues.

2. A chimeric photoprotein according to claim 1, wherein said corresponding region of Clytin photoprotein is the same corresponding region of the Obelin protein sequence that is to be replaced with the exception of 1 amino acid residue.

3. A chimeric photoprotein according to claim 1, wherein said region extends from residue 50 to 94 of Obelin protein sequence as set forth in SEQ ID NO: 2.

4. A chimeric photoprotein according to claim 3, having the amino acid sequence of SEQ ID NO: 3.

5. A fusion protein containing the photoprotein of claim 1.

6. A conjugation product between the photoprotein according to claim 1 and a molecule for analytical, diagnostic or therapeutic use.

7. An isolated nucleic acid molecule encoding the chimeric photoprotein according to claim 1.

8. An isolated nucleic acid molecule according to claim 7, encoding the protein, having a sequence selected from SEQ ID NO: 4 and SEQ ID NO: 5.

9. A method for detecting calcium ions, comprising contacting a luciferin substrate with a cell expressing the chimeric photoprotein according to claim 1.

10. The method according to claim 9, wherein said luciferin substrate is coelenterazine.

11. The method according to claim 9, further comprising determining the quantity of calcium ions.

12. The method according to claim 9, further comprising determining intracellular calcium concentration.

13. An isolated host cell comprising the nucleic acid molecule according to claim 7.

14. The host cell of claim 13, which is selected from bacterial, yeast, fungal, plant, insect and animal cells.

15. A method for producing a photoprotein, which comprises growing the host cell of claim 13 in conditions suitable for photoprotein expression, and recovering the expressed protein.

16. A method for the screening of biologically active molecules, which comprises combining said molecules with a culture of host cells according to claim 13, and determining the intracellular calcium concentration.

17. A method according to claim 16, wherein the host cells are transfected a heterologous G-protein coupled receptor or ion channel.

18. A method for determining the amount of a molecule for analytical, diagnostic or therapeutic use, comprising subjecting the conjugation product according to claim 6 to a competitive solid-phase immunoassay, and determining the amount of said molecule.

19. A bioluminescence resonance energy transfer (BRET) system, comprising a fluorescent protein and the photoprotein of claim 4.

* * * * *

SEQUENCE LISTING

```
<160> NUMBER OF SEQ ID NOS: 9

<210> SEQ ID NO 1
<211> LENGTH: 662
<212> TYPE: DNA
<213> ORGANISM: Obelia longissima

<400> SEQUENCE: 1
acgatcgaac caaacaactc agctcacagc tactgaacaa ctcttgttgt gtacaatcaa      60
aatgtcttca aaatacgcag ttaaactcaa gactgacttt gataatccac gatggatcaa     120
aagacacaag cacatgtttg atttcctcga catcaatgga aatggaaaaa tcaccctcga     180
tgaaattgtg tccaaggcat ctgatgacat atgtgccaag ctcgaagcca caccagaaca     240
aacaaaacgc catcaagttt gtgttgaagc tttctttaga ggatgtggaa tggaatatgg     300
taaagaaatt gccttcccac aattcctcga tggatggaaa caattggcga cttcagaact     360
caagaaatgg gcaagaaacg aacctactct cattcgtgaa tggggagatg ctgtctttga     420
tattttcgac aaagatggaa gtggtacaat cactttggac gaatggaaag cttatggaaa     480
```

```
aatctctggt atctctccat cacaagaaga ttgtgaagcg acatttcgac attgcgattt      540
ggacaacagt ggtgaccttg atgttgacga gatgacaaga caacatcttg gattctggta      600
cactttggac ccagaagctg atggtctcta tggcaacgga gttccctaag cttttttcg       660 aa                                                                     662
```

```
<210> SEQ ID NO 2
<211> LENGTH: 195
<212> TYPE: PRT
<213> ORGANISM: Obelia longissima

<400> SEQUENCE: 2

Met Ser Ser Lys Tyr Ala Val Lys Leu Lys Thr Asp Phe Asp Asn Pro
  1               5                  10                  15

Arg Trp Ile Lys Arg His Lys His Met Phe Asp Phe Leu Asp Ile Asn
                 20                  25                  30

Gly Asn Gly Lys Ile Thr Leu Asp Glu Ile Val Ser Lys Ala Ser Asp
             35                  40                  45

Asp Ile Cys Ala Lys Leu Glu Ala Thr Pro Glu Gln Thr Lys Arg His
 50                  55                  60

Gln Val Cys Val Glu Ala Phe Phe Arg Gly Cys Gly Met Glu Tyr Gly
 65                  70                  75                  80

Lys Glu Ile Ala Phe Pro Gln Phe Leu Asp Gly Trp Lys Gln Leu Ala
                 85                  90                  95

Thr Ser Glu Leu Lys Lys Trp Ala Arg Asn Glu Pro Thr Leu Ile Arg
            100                 105                 110

Glu Trp Gly Asp Ala Val Phe Asp Ile Phe Asp Lys Asp Gly Ser Gly
            115                 120                 125

Thr Ile Thr Leu Asp Glu Trp Lys Ala Tyr Gly Lys Ile Ser Gly Ile
130                 135                 140

Ser Pro Ser Gln Glu Asp Cys Glu Ala Thr Phe Arg His Cys Asp Leu
145                 150                 155                 160

Asp Asn Ser Gly Asp Leu Asp Val Asp Glu Met Thr Arg Gln His Leu
                165                 170                 175

Gly Phe Trp Tyr Thr Leu Asp Pro Glu Ala Asp Gly Leu Tyr Gly Asn
            180                 185                 190

Gly Val Pro
        195

<210> SEQ ID NO 3
<211> LENGTH: 195
<212> TYPE: PRT
<213> ORGANISM: Artificial Sequence
<220> FEATURE:
<223> OTHER INFORMATION: Description of Artificial Sequence: Synthetic
      chimeric protein sequence

<400> SEQUENCE: 3

Met Ser Ser Lys Tyr Ala Val Lys Leu Lys Thr Asp Phe Asp Asn Pro
  1               5                  10                  15

Arg Trp Ile Lys Arg His Lys His Met Phe Asp Phe Leu Asp Ile Asn
                 20                  25                  30

Gly Asn Gly Lys Ile Thr Leu Asp Glu Ile Val Ser Lys Ala Ser Asp
             35                  40                  45

Asp Ile Cys Ala Lys Leu Gly Ala Thr Pro Glu Gln Thr Lys Arg His
 50                  55                  60
```

```
Gln Asp Ala Val Glu Ala Phe Phe Lys Lys Ile Gly Met Asp Tyr Gly
 65                  70                  75                  80

Lys Glu Val Glu Phe Pro Ala Phe Val Asp Gly Trp Lys Glu Leu Ala
                 85                  90                  95

Thr Ser Glu Leu Lys Lys Trp Ala Arg Asn Glu Pro Thr Leu Ile Arg
            100                 105                 110

Glu Trp Gly Asp Ala Val Phe Asp Ile Phe Asp Lys Asp Gly Ser Gly
        115                 120                 125

Thr Ile Thr Leu Asp Glu Trp Lys Ala Tyr Gly Lys Ile Ser Gly Ile
    130                 135                 140

Ser Pro Ser Gln Glu Asp Cys Glu Ala Thr Phe Arg His Cys Asp Leu
145                 150                 155                 160

Asp Asn Ser Gly Asp Leu Asp Val Asp Glu Met Thr Arg Gln His Leu
                165                 170                 175

Gly Phe Trp Tyr Thr Leu Asp Pro Glu Ala Asp Gly Leu Tyr Gly Asn
            180                 185                 190

Gly Val Pro
        195

<210> SEQ ID NO 4
<211> LENGTH: 600
<212> TYPE: DNA
<213> ORGANISM: Artificial Sequence
<220> FEATURE:
<223> OTHER INFORMATION: Description of Artificial Sequence: Synthetic
      chimeric nucleotide sequence

<400> SEQUENCE: 4
ggatccgccg ccatgtcttc aaaatacgca gttaaactca agactgactt tgataatcca      60
cgatggatca aaagacacaa gcacatgttt gatttcctcg acatcaatgg aaatggaaaa     120
atcaccctcg atgaaattgt gtccaaggca tctgatgaca tatgcgccaa acttggagca     180
acaccagaac agaccaaacg tcaccaggat gctgtcgaag ctttcttcaa aaagattggt     240
atggattatg gtaaagaagt cgaattccca gcttttgttg atggatggaa agaattggcg     300
acttcagaac tcaagaaatg gcaagaaacg aacctactc tcattcgtga atggggagat      360
gctgtctttg atattttcga caaagatgga agtggtacaa tcactttgga cgaatggaaa     420
gcttatggaa aaatctctgg tatctctcca tcacaagaag attgtgaagc gacatttcga     480
cattgcgatt tggacaacag tggtgacctt gatgttgacg agatgacaag acaacatctt     540
ggattctggt acactttgga cccagaagct gatggtctct atggcaacgg agttccctaa     600

<210> SEQ ID NO 5
<211> LENGTH: 607
<212> TYPE: DNA
<213> ORGANISM: Artificial Sequence
<220> FEATURE:
<223> OTHER INFORMATION: Description of Artificial Sequence: Synthetic
      chimeric nucleotide sequence

<400> SEQUENCE: 5
ggatccgccg ccatgtcttc aaaatacgca gttaaactca agactgactt tgataatcca      60
cgatggatca aaagacacaa gcacatgttt gatttcctcg acatcaatgg aaatggaaaa     120
atcaccctcg atgaaattgt gtccaaggca tctgatgaca tctgcgccaa actgggagca     180
acaccagaac agaccaaacg gcaccaggat gctgtcgaag ctttcttcaa aaagattggt     240
atggattatg gtaaagaagt cgaattccca gcttttgttg atggatggaa agaattggcg     300
```

```
acttcagaac tcaagaaatg ggcaagaaac gaacctactc tcattcgtga atggggagat      360
gctgtctttg atattttcga caaagatgga agtggtacaa tcactttgga cgaatggaaa      420
gcttatggaa aaatctctgg tatctctcca tcacaagaag attgtgaagc gacatttcga      480
cattgcgatc tggacaacag tggcgacctg gatgttgact agatgacaag acaacatctt      540
ggattctggt acactttgga cccagaagct gatggcctct atggcaacgg agttccctaa      600
gaattcc                                                                607

<210> SEQ ID NO 6
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tatgcgccaa acttggagca acaccagaac agaccaaacg tcaccaggat gctgtcgaag       60
ctttcttcaa                                                              70

<210> SEQ ID NO 7
<211> LENGTH: 71
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
tttttgaaga aagcttcgac agcatcctgg tgacgtttgg tctgttctgg tgttgctcca       60
agtttggcgc a                                                            71

<210> SEQ ID NO 8
<211> LENGTH: 62
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
aaagattggt atggattatg gtaaagaagt cgaattccca gcttttgttg atggatggaa       60
ag                                                                      62

<210> SEQ ID NO 9
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aattctttcc atccatcaac aaaagctggg aattcgactt ctttaccata atccatacca       60
atc                                                                     63
```